(12) United States Patent
Jiang et al.

(10) Patent No.: US 12,150,992 B2
(45) Date of Patent: Nov. 26, 2024

(54) MULTIFUNCTIONAL THERAPEUTIC BIOLOGICAL MATERIAL AND PREPARATION METHOD THEREOF

(71) Applicant: BEIJING INSTITUTE OF TECHNOLOGY, Beijing (CN)

(72) Inventors: Lan Jiang, Beijing (CN); Yunlong Ma, Beijing (CN); Jie Hu, Beijing (CN)

(73) Assignee: BEIJING INSTITUTE OF TECHNOLOGY, Beijing (CN)

( * ) Notice: Subject to any disclaimer, the term of this patent is extended or adjusted under 35 U.S.C. 154(b) by 657 days.

(21) Appl. No.: 17/492,060

(22) Filed: Oct. 1, 2021

(65) Prior Publication Data
US 2022/0313821 A1    Oct. 6, 2022

(30) Foreign Application Priority Data

Apr. 6, 2021   (CN) .......................... 202110367535.2

(51) Int. Cl.
*A61L 27/54*     (2006.01)
*A61K 41/00*     (2020.01)
(Continued)

(52) U.S. Cl.
CPC .......... *A61K 41/0052* (2013.01); *A61L 27/06* (2013.01); *A61L 27/54* (2013.01);
(Continued)

(58) Field of Classification Search
CPC .. A61L 27/54; A61L 2400/12; A61L 2430/02; B82Y 5/00
See application file for complete search history.

(56) References Cited

U.S. PATENT DOCUMENTS

| 7,005,669 B1 * | 2/2006 | Lee | ........................ | B82Y 20/00 |
| | | | | 257/17 |
| 10,203,325 B2 * | 2/2019 | Alocilja | .................. | C23C 18/44 |

(Continued)

FOREIGN PATENT DOCUMENTS

| CN | 102732898 | 10/2012 |
| CN | 102974375 | 3/2013 |

(Continued)

OTHER PUBLICATIONS

Fekrazad, Reza, et al., "The Combination of Laser Therapy and Metal Nanoparticles in Cancer Treatment Originated From Epithelial Tissues: A Literature Review". Journal of Laser in Medical Sciences, Spring 2016; 7(2): 62-75.*

(Continued)

*Primary Examiner* — Bret P Chen
(74) *Attorney, Agent, or Firm* — Norton Rose Fulbright US LLP

(57) ABSTRACT

The present disclosure relates to a multifunctional therapeutic biological material and preparation method thereof. The process steps of the preparation method are as follows: (1) preparing various three-dimensional micro/nano composite structure on the surface of a biomedical material by using femtosecond laser double pulses; (2) further preparing a nano-flower structure on the three-dimensional micro/nano composite structure by using hydrothermal synthesis method to construct a heterogeneous structure consisting of the three-dimensional micro/nano composite structure and the nano-flower structure; (3) putting the prepared heterogeneous structure into a mixed solution containing gold ions and platinum ions, and by using ultraviolet light reduction method, reducing in situ into gold-platinum bimetallic nanoparticles on the heterogeneous structure to obtain the multifunctional therapeutic biological material. The multifunctional therapeutic biological material provided by the (Continued)

present disclosure has excellent light-to-heat conversion characteristics, and it can promote bone regeneration, and has functions of tumor treatment and anti-bacterial infection.

11 Claims, 7 Drawing Sheets

(51) Int. Cl.
    *A61L 27/06*     (2006.01)
    *A61P 35/00*     (2006.01)
    *B82Y 5/00*      (2011.01)
    *B82Y 30/00*     (2011.01)
    *B82Y 40/00*     (2011.01)
    *C23C 18/42*     (2006.01)

(52) U.S. Cl.
    CPC ......... *A61P 35/00* (2018.01); *A61L 2300/104* (2013.01); *A61L 2400/06* (2013.01); *A61L 2400/12* (2013.01); *A61L 2430/02* (2013.01); *B82Y 5/00* (2013.01); *B82Y 30/00* (2013.01); *B82Y 40/00* (2013.01); *C23C 18/42* (2013.01)

(56) References Cited

U.S. PATENT DOCUMENTS

| | | | | |
|---|---|---|---|---|
| 2001/0043495 | A1* | 11/2001 | Kumacheva | G11B 7/245 |
| 2010/0070197 | A1* | 3/2010 | Wang | G01J 3/02 |
| | | | | 702/22 |
| 2010/0085564 | A1* | 4/2010 | Guo | G01J 3/021 |
| | | | | 977/773 |
| 2012/0219624 | A1* | 8/2012 | Ko | A61K 38/193 |
| | | | | 424/490 |
| 2013/0034854 | A1* | 2/2013 | Ashworth-Sharpe | C07F 9/65522 |
| | | | | 977/920 |
| 2013/0183833 | A1 | 7/2013 | Duan et al. | |
| 2016/0035916 | A1* | 2/2016 | Wong | H01L 31/022466 |
| | | | | 252/512 |
| 2017/0057839 | A1* | 3/2017 | Atieh | B01J 20/08 |

FOREIGN PATENT DOCUMENTS

| | | |
|---|---|---|
| CN | 108079383 | 5/2018 |
| CN | 108555437 | 9/2018 |
| CN | 109730802 | 5/2019 |
| CN | 110116273 | 8/2019 |
| CN | 110433737 | 11/2019 |
| CN | 112170841 | 1/2021 |
| CN | 112198567 | 1/2021 |
| JP | 2013539911 | 10/2013 |

OTHER PUBLICATIONS

Bayazitoglu, Yildiz, et al., "An overview of nanoparticle assisted laser therapy". International Journal of Heat and Mass Transfer 67 ( 2013) 469-486.*

Mesicek, Jakub, et al., "Summary of numerical analyses for therapeutic uses of laser-activated gold nanoparticles". International Journal of Hyperthermia 2018, vol. 34, No. 8, 1255-1264.*

Vines, Jeremy B., et al., "Gold Nanoparticles for Photothermal Cancer Therapy". Frontiers in Chemistry, Apr. 2019, vol. 7, Article 167, pp. 1-16.*

Office Action issued in corresponding Chinese Application No. 202110367535.2, dated Nov. 22, 2021.

* cited by examiner

FIG. 7

MULTIFUNCTIONAL THERAPEUTIC BIOLOGICAL MATERIAL AND PREPARATION METHOD THEREOF

CROSS-REFERENCE TO RELATED APPLICATIONS

This application claims the benefit of priority to Chinese Patent Application No. 202110367535.2, entitled "MULTIFUNCTIONAL THERAPEUTIC BIOLOGICAL MATERIAL AND PREPARATION METHOD THEREOF," filed on Apr. 6, 2021, with the China National Intellectual Property Administration, which is incorporated herein by reference in its entirety.

FIELD OF THE INVENTION

The present disclosure relates to a multifunctional therapeutic biological material and preparation method thereof, which has the functions of treating tumors, bacterial infections and repairing bone defects, and belongs to the field of laser application technology.

BACKGROUND OF THE INVENTION

Bone tumor, a common malignant tumor, is one of the most harmful tumors with high mortality and a serious threat to human health worldwide. Except for autologous skeletal system cancer, bone metastasis is a fatal cancer complication that occurs in 30%-80% of cancer patients. For example, up to 65%-80% of patients with advanced breast and prostate cancer are diagnosed with bone metastases, and nearly 50% of patients with colon cancer, the world's third most common cancer, will eventually develop bone metastases. At present, the mainstream clinical treatment of bone tumors is mostly a combination of destructive surgical resection and chemotherapy/radiotherapy, which significantly improves the survival rate of patients. However, the tumor recurrence, large-area bone defect, and postoperative bacterial infections (infection rate of 20%-50%) associated with post-surgical resection of bone tumors are serious problems that still threaten the health of patients. Chemotherapy/radiotherapy has been widely used to kill surviving tumor cells after surgery, but drug resistance and various serious systemic side effects continue to afflict patients. Therefore, there is still an urgent clinical need for a multifunctional therapeutic biological material for post-bone tumor surgery, which can not only meet the needs of bone defect filling and guide bone tissue regeneration, but also remove residual tumor cells and prevent bacterial infections in a safe and effective way. However, there are very limited multifunctional therapeutic biological materials that have properties of bone defect repair, tumor treatment, and anti-bacterial infection in current clinical practice.

In recent years, photothermal therapy has received more and more attention due to its non-invasive, effective and non-toxic side effects. The heat generated by absorbing near-infrared light is used to kill tumor cells in the targeted area and prevent damage to the non-targeted area. Compared with chemotherapy/radiotherapy, it has obvious advantages, such as less invasiveness, and rapid recovery of tissues in the treated area. Therefore, the combination of biomedical materials with bone regeneration properties and photothermal therapy is expected to be effective in bone defect repair, tumor treatment and anti-bacterial infection at the same time. Of note, it is particularly important to select photothermal materials with significant photothermal effects and high biocompatibility for the preparation of multifunctional therapeutic biological materials.

In the current prior art, for example, Chinese Patent CN 108555437 A discloses a laser processing method for directional regulation of cell growth on the surface of biological metal materials, but it focuses on the osteogenic properties of the material and does not involve tumor treatment and anti-bacterial infection. For another example, Chinese patent CN 108079383 A discloses a photothermal bone repair scaffold prepared by using the photothermal effect of carbon quantum dots and the osteogenesis properties of hydroxyapatite, but carbon-based nanomaterials can cause lung inflammation and oxidative stress on patients, thus with low biological safety in vivo. In summary, it is imperative to invent a multifunctional therapeutic biological material with universal, low-cost, high biocompatibility, long-term durability, and functions of bone defect repair, tumor treatment, and anti-bacterial infection.

SUMMARY OF THE INVENTION

The purpose of the present disclosure is to solve the severe problems of tumor recurrence, large-area bone defect and postoperative bacterial infections associated with post-surgical resection of bone tumors, and to provide a multifunctional therapeutic biological material, which aims to solve the above-mentioned major challenges faced by the post-surgical resection of bone tumors.

The purpose of the present disclosure is specifically achieved through the following technical solutions:

The present disclosure provides a method for preparing a multifunctional therapeutic biological material, comprising:

Step 1: Performing mirror polishing pretreatment on the surface of a biomedical material to be processed, ultrasonically cleaning it and drying it, to obtain a clean surface polishing material.

Step 2: Preparing a large-area and consistent three-dimensional micro/nano composite structure on the surface of the surface polishing material obtained in step 1 by using femtosecond laser, cleaning the processed material with deionized water and drying it.

Step 3: Preparing a nano-flower structure on the surface of the material obtained in step 2, and constructing a heterogeneous structure consisting of the three-dimensional micro/nano composite structure and the nano-flower structure.

Step 4: Putting the heterogeneous structure prepared in step 3 into a mixed solution containing gold ions and platinum ions, and by using ultraviolet light reduction method, reducing in situ into gold-platinum bimetallic nanoparticles on the heterogeneous structure to obtain the multifunctional therapeutic biological material.

The present disclosure provides a use of a product prepared by the method for treating tumors and bacterial infections, and repairing bone defects, and specifically, for treating bone tumor and postoperative bacterial infection.

The biomedical material in step 1 comprises a medical metal material, medical ceramic material, medical polymer material, and medical non-metal material.

The specific implementation steps of step 2 comprises:

(1) Fixing the clean surface polishing material on a glass slide, and fixing the glass slide on a high-precision six-degree-of-freedom translation stage;

(2) Modulating the traditional femtosecond laser into femtosecond laser double pulses in the time domain through splitting and combining or pulse shaping, with a time interval between two sub-pulses of 100 fs-100 ps and an energy ratio range of two sub-pulses of 0.1-10;

(3) Focusing the generated femtosecond laser double pulses on the surface of the surface polishing material by using an objective lens, and making sample move relative to the laser by controlling the high-precision six-degree-of-freedom translation stage through a computer control system; during processing, using high-pressure nitrogen for blowing chips and controlling laser flux, processing speed, processing distance, and double pulse delay time to prepare the three-dimensional micro/nano composite structure; and (4) Cleaning the material after the above processing with deionized water and drying it.

The specific implementation steps of step 3 comprises:

(1) Preparing a mixed solution consisting of sodium hydroxide solution and hydrogen peroxide solution as a hydrothermal reaction system;

(2) Putting the biomedical material with a surface of the three-dimensional micro/nano composite structure prepared by the femtosecond laser double pulses processing into the bottom of a reactor, and then pouring the prepared mixed solution into the reactor for hydrothermal reaction; and (3) Cleaning the material after the hydrothermal reaction with deionized water and drying it.

The specific implementation steps of step 4 comprises:

(1) Preparing a mixed solution consisting of chloroauric acid and chloroplatinic acid as a precursor solution;

(2) Putting the biomedical material with a surface of the heterogeneous structure consisting of the three-dimensional micro/nano composite structure and the nano-flower structure prepared by the femtosecond laser double pulses processing combined with hydrothermal treatment into the bottom of a beaker, then adding the prepared precursor solution dropwise into the beaker, and finally placing an ultraviolet light source horizontally above the beaker for irradiation; and (3) Cleaning the material after photoreduction reaction with deionized water and drying it.

In step 2 (3), the multiple of the objective lens, laser flux, processing speed, processing distance, and double pulse delay time are 5 times, 10 times or 20 times, 1-150 J/cm$^2$, 10-2000 μm/s, 2-30 μm and 5-20 ps respectively.

In step 3 (1), the concentration of the sodium hydroxide solution is 1-20 mM, and the concentration of the hydrogen peroxide solution is 5%-30%.

In step 3 (2), the temperature of the hydrothermal reaction is 50-120° C., and the reaction time is 24-48 h.

In step 4 (1), the concentrations of the chloroauric acid and the chloroplatinic acid in step (1) are both 10-50 mM, and the two solutions are mixed at 1:1 as the precursor solution.

In step 4 (2), the power of the ultraviolet light source is 5-20 W, and the photoreduction process time is 10-30 s.

The present disclosure provides a method for treating tumors and bacterial infections and repairing bone defects, comprising administering to a subject in need thereof the multifunctional therapeutic biological material prepared by the above method.

The present disclosure provides a method for treating bone tumors and postoperative bacterial infections, comprising administering to a subject in need thereof the multifunctional therapeutic biological material prepared by the above method.

Beneficial Effect (1) The present disclosure provides a multifunctional therapeutic biological material, wherein the multifunctional therapeutic biological material has the functions of treating tumors, bacterial infections, and repairing bone defects, and can be used to treat bone tumors and postoperative bacterial infections.

(2) The present disclosure provides a method for preparing the multifunctional therapeutic biological material, wherein the method has a patterning processing capability, which can be used for biomedical materials of various sizes and different shapes.

(3) The present disclosure provides a multifunctional therapeutic biological material and preparation method thereof, wherein the multifunctional therapeutic biological material has excellent light-to-heat conversion characteristics in vitro or in vivo.

(4) The present disclosure provides a multifunctional therapeutic biological material and preparation method thereof, wherein the multifunctional therapeutic biological material has excellent blood compatibility.

(5) The present disclosure provides a multifunctional therapeutic biological material and preparation method thereof, wherein the multifunctional therapeutic biological material has excellent cell compatibility in vitro and has no cytotoxicity.

(6) The present disclosure provides a multifunctional therapeutic biological material and preparation method thereof, wherein the multifunctional therapeutic biological material can significantly ablate human osteoblastic sarcoma cells (Saos-2) and human breast cancer cells (MDA-MB-231, a cancer cell prone to bone metastasis) through photothermal effect in vitro.

(7) The present disclosure provides a multifunctional therapeutic biological material and preparation method thereof, wherein the multifunctional therapeutic biological material has excellent biocompatibility in animals and has no systemic toxicity.

(8) The present disclosure provides a multifunctional therapeutic biological material and preparation method thereof, wherein the multifunctional therapeutic biological material can significantly inhibit the growth of bone tumors in vivo.

(9) The present disclosure provides a multifunctional therapeutic biological material and preparation method thereof, wherein tumor-bearing mice treated with the multifunctional therapeutic biological material maintain a 100% survival rate after 60 days of rearing, and develop no tumor recurrence.

(10) The present disclosure provides a multifunctional therapeutic biological material and preparation method thereof, wherein the multifunctional therapeutic biological material significantly induces bone regeneration.

(11) The present disclosure provides a multifunctional therapeutic biological material and preparation method thereof, wherein the multifunctional therapeutic biological material can effectively inhibit the formation of biofilms, and can significantly kill various bacteria that adhere to the surface of the material through the photothermal effect, and thus has excellent anti-infection ability.

(12) The present disclosure provides a multifunctional therapeutic biological material and preparation method thereof, wherein the preparation method of the multifunctional therapeutic biological material is flexible and simple with the process parameters easy to control, and it is easy to realize the application in the field of laser technology. It is worth noting that this method does not need addition of any other stabilizers or auxiliary reducing agents during the ultraviolet light reduction process, and the material after the reduction is cleaned with deionized water and dried to obtain the multifunctional therapeutic biological material.

BRIEF DESCRIPTION OF THE DRAWINGS

FIG. 7 shows the toxicity test of the multifunctional therapeutic biological material prepared in the examples of the present disclosure in an animal (nude mouse).

DETAILED DESCRIPTION

In order to better understand the present disclosure, the technical solutions of the present disclosure will be further described in detail below in conjunction with specific embodiments.

Unless otherwise specified, the experimental methods used in the following examples are all conventional methods.

Example 1

The multifunctional therapeutic biological material and preparation method thereof of this example, comprising:

Step 1: Optically polishing nickel-titanium (NiTi) alloy to obtain a mirror-polished nickel-titanium (NiTi) alloy sample with a surface roughness of less than 5 angstroms.

Step 2: Cleaning the mirror-polished titanium alloy sample in step 1 with an ultrasonic cleaner at an ultrasonic frequency of 80 KHZ, and submerging the surface of the sample with deionized water followed by anhydrous ethanol solution for cleaning at room temperature for 3 min separately.

Step 3: Drying the cleaned titanium alloy sample in step 2 with cold air to obtain a clean titanium alloy sample.

Step 4: Performing laser-induced three-dimensional micro/nano composite structure processing on the titanium alloy surface using the femtosecond laser double pulses processing system shown in FIG. 1(a) and following the specific processing process shown in FIG. 1(b). The laser processing parameters are specifically set as follows: the wavelength of the femtosecond laser is 800 nm, the pulse duration is 35 fs, the repetition frequency is 1 KHZ, the processing objective lens is a 5× objective lens, the laser flux of the double pulses is 128.36 J/cm$^2$, the scanning speed is 1400 μm/s, the scanning distance is 5 and the pulse delay is 5 ps. Throughout the process, high-pressure nitrogen for blowing chips was used to process a large-area and consistent three-dimensional porous array micro/nano composite structure.

Figure 1:
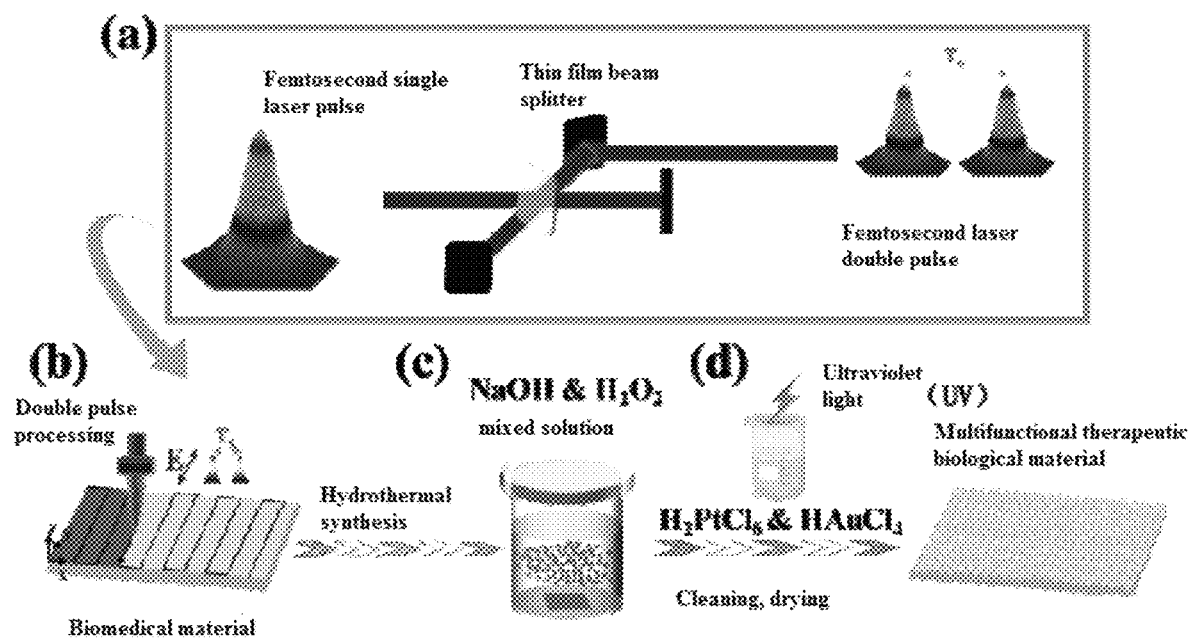
FIG. 1 shows a process flow diagram of preparing the multifunctional therapeutic biological material according to the examples of the present disclosure; wherein (a) shows a femtosecond laser double pulses processing system; (b) shows preparing a three-dimensional micro/nano composite structure on the surface of a biomedical material by using femtosecond laser double pulses; (c) shows the hydrothermal synthesis method; and (d) shows the ultraviolet light (UV) reduction method.
Figure 2:
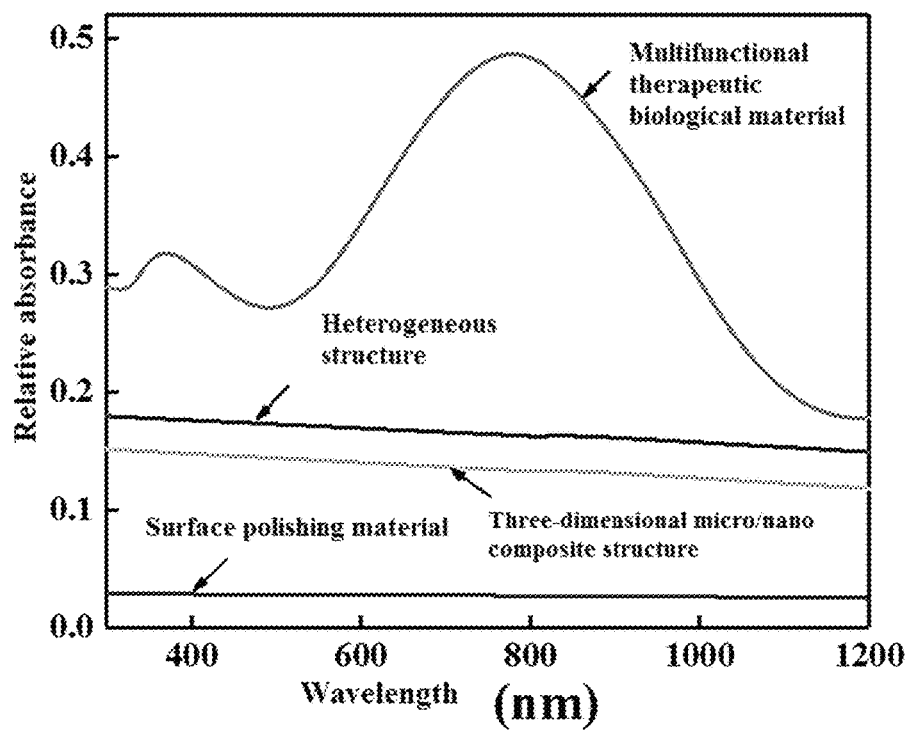
FIG. 2 shows an ultraviolet (UV)-visible light (vis)-near infrared (NIR) absorption spectrum of the multifunctional therapeutic biological material prepared in the examples of the present disclosure.

Step 5: By using the hydrothermal synthesis method shown in FIG. 1(c), further preparing a nano-flower structure on the three-dimensional porous array micro/nano composite structure of the titanium alloy sample with the surface of three-dimensional porous array micro/nano composite structure prepared by femtosecond laser double pulses processing, to construct a heterogeneous structure consisting of the three-dimensional porous array micro/nano composite structure and the nano-flower structure. The heterogeneous structure prepared by the present disclosure has unexpected technical effects as shown in FIG. 2, which shows the absorption spectrum of ultraviolet (UV)-visible light (vis)-near infrared (NIR) on different surfaces prepared in the above steps. First, it can be seen that the surface-polished material has no absorption characteristics in the entire ultraviolet to near-infrared band, but the three-dimensional micro/nano composite structure prepared by femtosecond laser processing significantly improves the absorptivity in the ultraviolet to near-infrared band, showing the slope characteristic of the highest absorptivity in the ultraviolet band. Secondly, the heterogeneous structure constructed by the hydrothermal method further improves the absorptivity in the ultraviolet to near-infrared band, also showing the slope characteristic of the highest absorptivity in the ultraviolet band. Therefore, the present disclosure has the technical characteristics of selective and strong absorption in the ultraviolet band by the heterogeneous structure. The experiment of the next step was performed.

Figure 3:
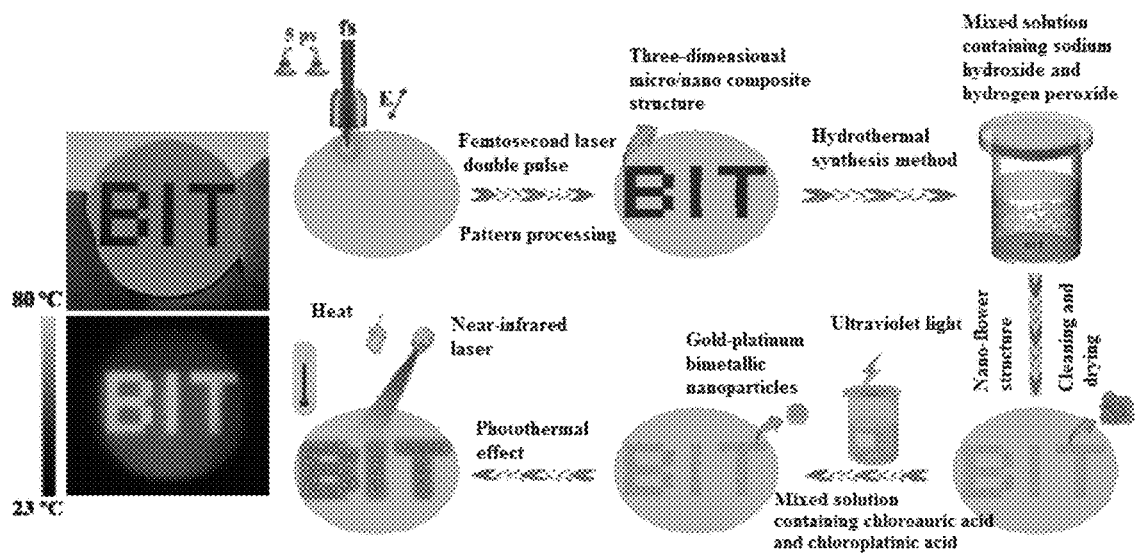
FIG. 3 shows a schematic diagram showing the patterning processing capability of the preparation method of the present disclosure.

Step 6. Putting the titanium alloy sample with a surface of the heterogeneous structure prepared in step 5 into a mixed solution consisting of chloroauric acid (HAuCl$_4$) and chloroplatinic acid (H$_2$PtCl$_6$), and reducing in situ into gold-platinum (AuPt) bimetallic nanoparticles on the heterogeneous structure by using the ultraviolet light (UV) reduction method as shown in FIG. 1(d), and cleaning the material after the reduction with deionized water and drying it to obtain the multifunctional therapeutic biological material. It is worth noting that this method does not need addition of any other stabilizers or auxiliary reducing agents during the reduction process. The ultraviolet (UV)-visible light (vis)-near infrared (NIR) absorption spectrum of the multifunctional therapeutic biological material is shown in FIG. 2. It can be seen that due to the localized surface plasmon resonance effect of the gold-platinum (AuPt) bimetallic nanoparticles, the multifunctional therapeutic biomaterial has excellent light absorption characteristics in the near-infrared band, so it can be used for near-infrared laser (808 nm)-assisted photothermal therapy. It is worth noting that the preparation method of the present disclosure can prepare heterogeneous structures with arbitrary patterns by the combination of femtosecond laser processing technology with hydrothermal synthesis method. By utilizing the technical characteristics of heterogeneous structures with selective and strong absorption in the ultraviolet band, the gold-platinum (AuPt) bimetallic nanoparticles can be produced by reduction in situ on the patterned heterogeneous structure, which is suitable for biomedical materials of various sizes and different shapes. The schematic diagram of the result display of the patterning processing capability possessed by the preparation method of the present disclosure is shown in FIG. 3.

Wherein, the hydrothermal synthesis method in step 5 comprises:

(1) Preparing 10 mL of 10 mM sodium hydroxide (NaOH) solution and 10 mL of 30% hydrogen peroxide ($H_2O_2$) solution respectively, and mixing the two fully as a hydrothermal reaction system;

(2) Putting the titanium alloy sample with a surface of the three-dimensional porous array micro/nano composite structure prepared by the femtosecond laser double pulses processing into the bottom of a polytetrafluoroethylene reactor with a stainless steel sleeve, and then pouring the prepared 20 mL mixed solution into the reactor, which is then placed in a vacuum drying oven at 80° C. for 48 h; and (3) After the hydrothermal reaction, taking out the titanium alloy sample, washing with deionized water, and drying to obtain a heterogeneous structure consisting of a three-dimensional porous array micro/nano composite structure and a nano-flower structure.

Wherein, the ultraviolet light (UV) reduction method described in step 6 comprises:

1) Preparing 5 mL of 50 mM chloroauric acid ($HAuCl_4$) and 5 mL of 50 mM chloroplatinic acid ($H_2PtCl_6$) respectively, and mixing the two fully at 1:1 as a precursor solution;

(2) Putting the titanium alloy sample with a surface of the heterogeneous structure consisting of the three-dimensional porous array micro/nano composite structure and the nano-flower structure prepared by the femtosecond laser double pulses processing combined with hydrothermal treatment into the bottom of a beaker, and then adding the prepared precursor solution dropwise into the beaker, and finally placing an ultraviolet (UV) light source horizontally above the beaker for irradiation with the power of the ultraviolet light source of 15 W and the irradiation time of 30 s; and (3) Cleaning the titanium alloy sample after photoreduction reaction with deionized water and drying it to obtain a multifunctional therapeutic biological material.

Wherein, in the photoreduction process described in step 6, the precursor solution can be placed in a plastic or glass beaker. Any photoreduction process carried out in different containers by using this method is within the scope of protection of this patent.

The product prepared by the method of the present disclosure has excellent functions of bone defect repair, tumor treatment, and anti-bacterial infection, and can be used to treat bone tumors and postoperative bacterial infections.

Figure 4:
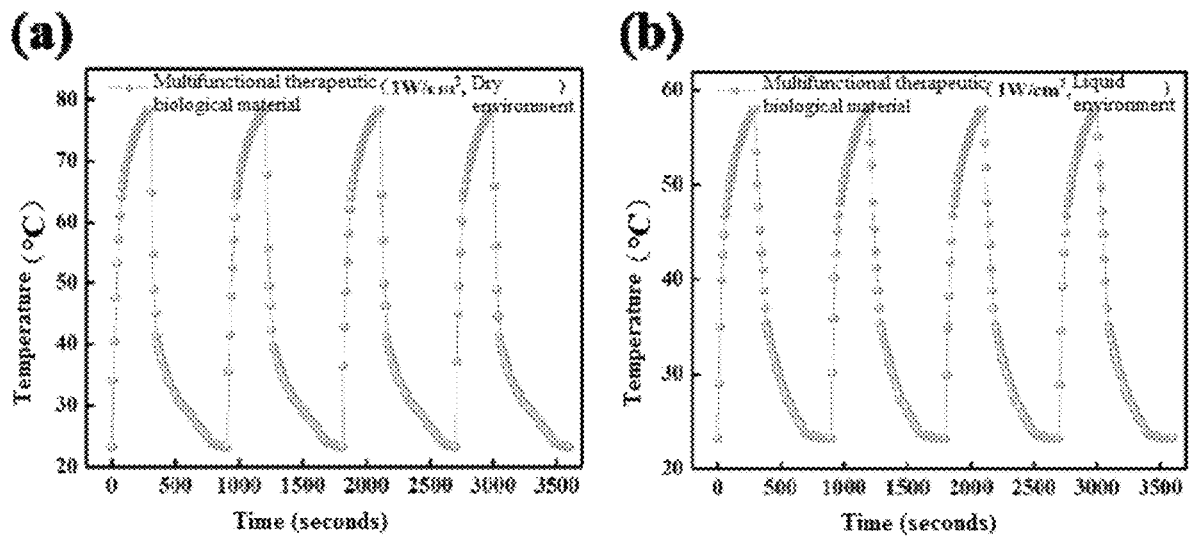
FIG. 4 shows the in vitro photothermal characteristics and stability (4 cycles of experiments) of the multifunctional therapeutic biological material prepared in the examples of the present disclosure using near-infrared (808 nm) laser irradiation; wherein (a) shows a dry (in the air) environment; and (b) shows a liquid (phosphate buffer) environment.

FIG. 4 shows the in vitro photothermal characteristics and stability (4 cycles of experiments) tests of the multifunctional therapeutic biological material prepared in the examples of the present disclosure. FIG. (a) shows that the multifunctional therapeutic biological material is irradiated with a near-infrared (808 nm) laser at a power density of 1.0 $W/cm^2$ in a dry (in the air) environment, and it can be seen that the surface temperature of the multifunctional therapeutic biological material rapidly increases to 78.5° C. within 5 minutes, and it has a stable photothermal effect under 4 cycles of experiments; and FIG. (b) shows that the multifunctional therapeutic biological material is irradiated with a near-infrared (808 nm) laser at a power density of 1.0 $W/cm^2$ in a liquid (phosphate buffer) environment, and it can be seen that the surface temperature of the multifunctional therapeutic biological material rapidly increases to 58.1° C. within 5 minutes, and it has a stable photothermal effect under 4 cycles of experiments. In summary, the multifunctional therapeutic biological material prepared in the examples of the present disclosure has excellent, controllable and stable photothermal effects in both dry and liquid environments.

Figure 5:
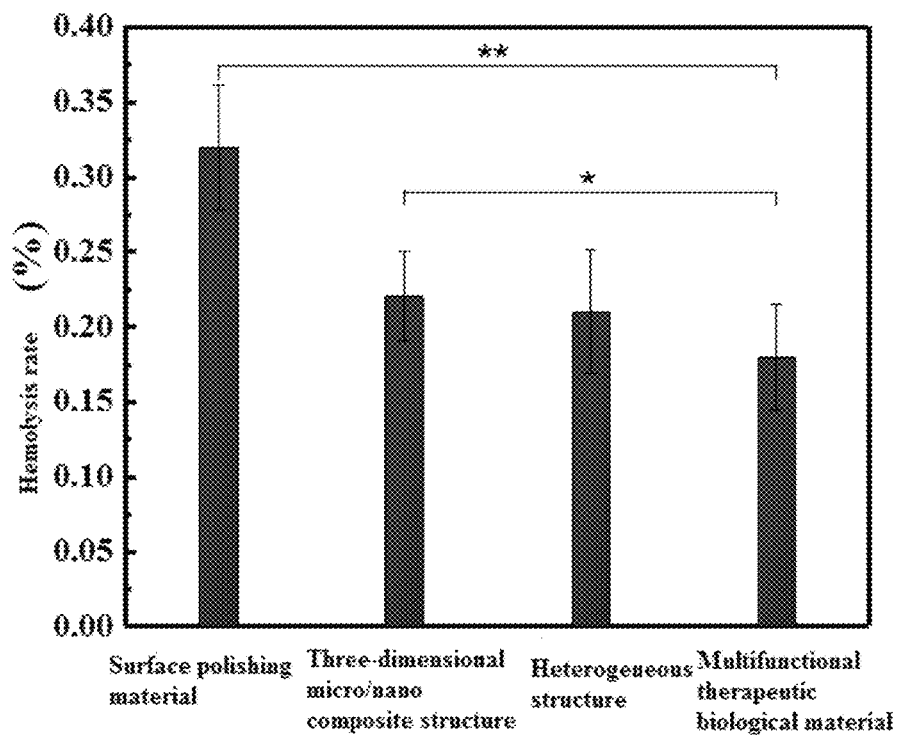
FIG. 5 shows the blood compatibility (hemolysis rate) of the multifunctional therapeutic biological material prepared in the examples of the present disclosure.

FIG. 5 shows the blood compatibility (hemolysis rate) of the multifunctional therapeutic biological material prepared in the examples of the present disclosure. It can be seen that the hemolysis rate of the multifunctional therapeutic biological material is only 0.18%, which is significantly lower than the internationally recognized standard value (5%), demonstrating that the multifunctional therapeutic biological material has almost no damage to red blood cells. In summary, the multifunctional therapeutic biological material prepared in the examples of the present disclosure can be safely applied in the medical field.

Figure 6:
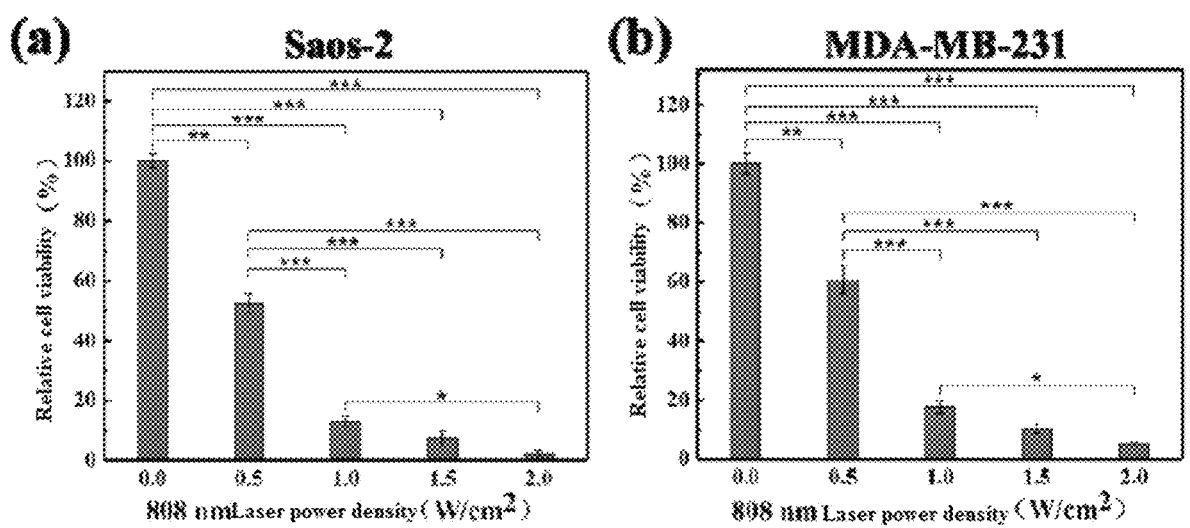
FIG. 6 shows the in vitro photothermal anti-cancer properties of the multifunctional therapeutic biological material prepared in the examples of the present disclosure; wherein (a) shows the relative cell viability of human osteoblastic sarcoma cells (Saos-2) as a function of power density changes of near-infrared (808 nm) laser irradiation (continuous irradiation for 10 min); and (b) shows the relative cell viability of human breast cancer cells (MDA-MB-231) as a function of power density changes of near-infrared (808 nm) laser irradiation (continuous irradiation for 10 min).

FIG. 6 shows the in vitro photothermal anti-cancer properties of the multifunctional therapeutic biological material prepared in the examples of the present disclosure. FIG. (a) shows the relative cell viability of human osteoblastic sarcoma cells (Saos-2) as a function of power density changes of near-infrared (808 nm) laser irradiation (continuous irradiation for 10 min);

FIG. (b) shows the relative cell viability of human breast cancer cells (MDA-MB-231) as a function of power density changes of near-infrared (808 nm) laser irradiation (continuous irradiation for 10 min). It can be seen that the activity of these two kinds of cancer cells will be significantly reduced with the increase of laser power density, indicating that the multifunctional therapeutic biological material prepared in the examples of the present disclosure has excellent in vitro photothermal anti-cancer properties.

Figure 7:
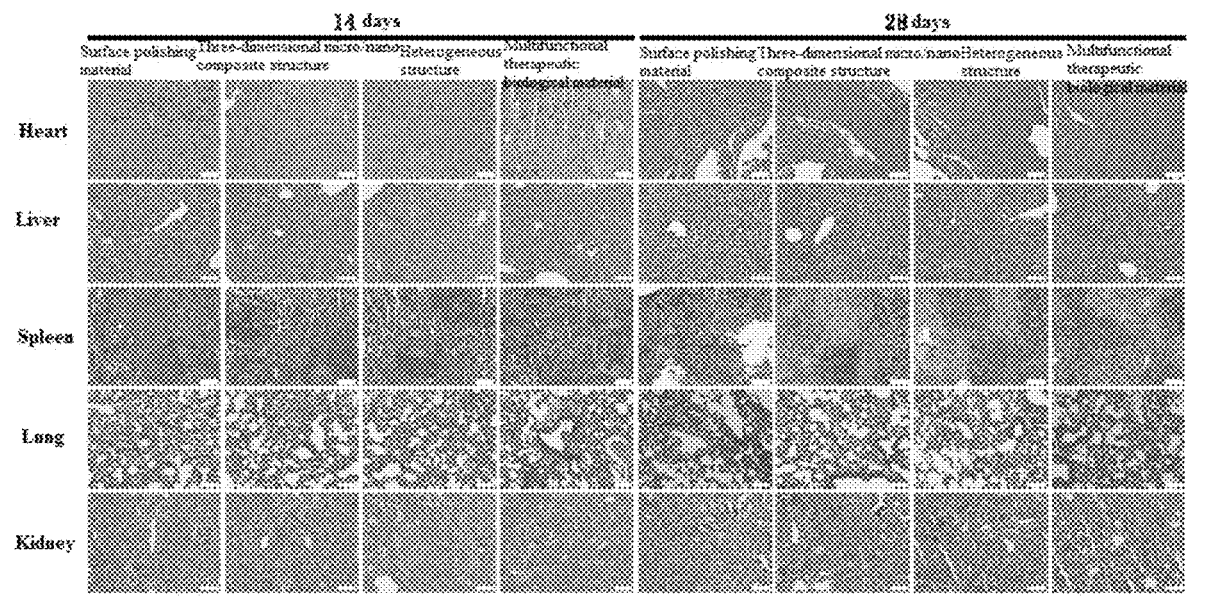

FIG. 7 shows the toxicity test of the multifunctional therapeutic biological material prepared in the examples of the present disclosure in an animal (nude mouse). After raising the nude mice implanted with the multifunctional therapeutic biological material for 14 and 28 days, the main organs (heart, liver, spleen, lung and kidney) of nude mice were taken out and subjected to H&E staining for histological analysis. It can be seen that no matter if it was reared for 14 days or 28 days, no obvious acute or chronic pathological toxicity and adverse reactions were seen in each organ. In summary, the multifunctional therapeutic biological material prepared in the examples of the present disclosure did not cause obvious histological abnormalities or lesions in animals.

Figure 8:
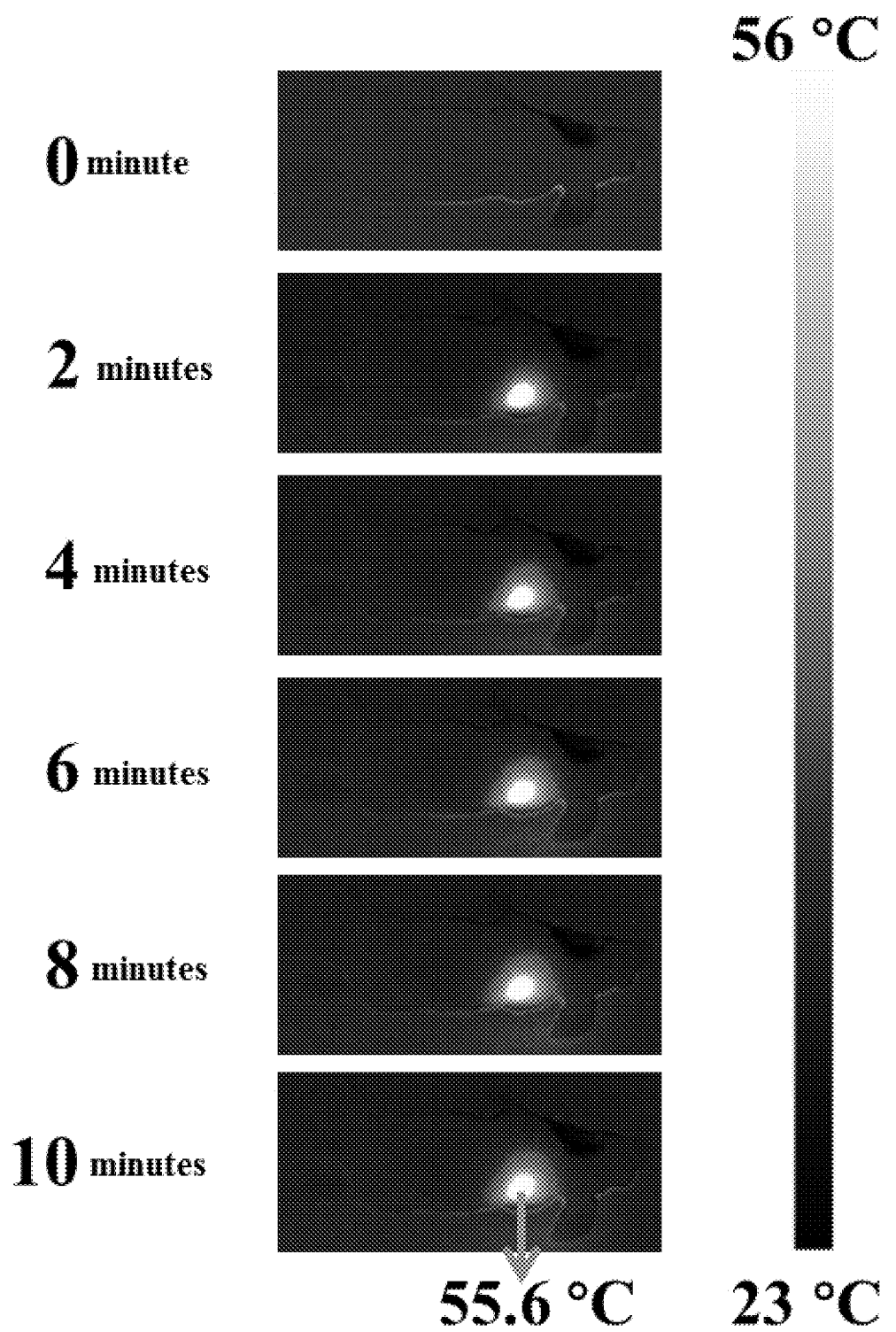
FIG. 8 shows the photothermal characteristics of the multifunctional therapeutic biological material prepared in the examples of the present disclosure in an animal (nude mouse) (laser power is 1 W/cm$^2$).

FIG. 8 shows the photothermal characteristics of the multifunctional therapeutic biological material prepared in the examples of the present disclosure in an animal (nude mouse) (laser power is 1 W/cm$^2$). It can be seen that the local temperature of the material implantation site rapidly increased to 58.1° C. within 10 min, indicating that the multifunctional therapeutic biological material prepared in the examples of the present disclosure has excellent, controllable and stable photothermal characteristic in the animal body.

Figure 9:
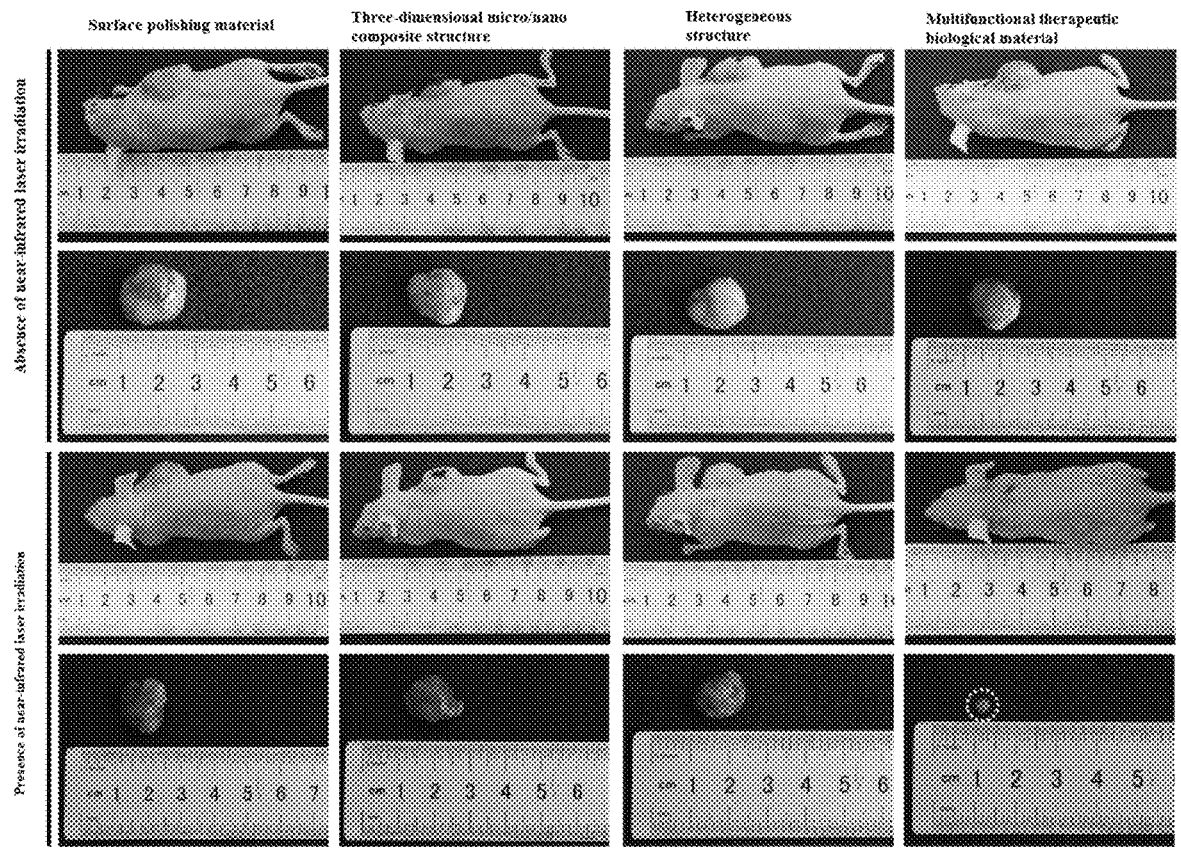
FIG. 9 shows the ability of the multifunctional therapeutic biological material prepared in the examples of the present disclosure to treat tumors in an animal (nude mice) with photothermal treatment.

FIG. 9 shows the ability of the multifunctional therapeutic biological material prepared in the examples of the present disclosure to treat tumors in an animal (nude mice) with photothermal treatment. First, the ectopic bone tumor model was established on the right side of the back of nude mice. When the diameter of the tumor was about 10 mm, the material was implanted at the bottom of the tumor. Then the nude mice were divided into no-treatment group and treatment group, where the nude mice in the no-treatment group were reared for 14 days after material implantation, while the nude mice in the treatment group were irradiated with near-infrared laser at the tumor site after material implantation, with a laser power density of 1 W/cm$^2$ and an irradiation time of 10 min a day for 3 days of continuous irradiation, and then reared for 14 days. It can be seen that when there is no near-infrared laser irradiation, surface polishing materials, materials with a three-dimensional micro/nano composite structure on the surface, materials with a heterogeneous structure on the surface, and the multifunctional therapeutic biological materials do not have therapeutic ability in nude mice reared for 14 days, whose tumor volume has shown a significant increase. When near-infrared laser irradiation treatment was performed, because surface polishing materials, materials with a three-dimensional micro/nano composite structure on the surface, and materials with a heterogeneous structure on the surface do not have photothermal properties in nude mice, the tumor volume still showed a significant increase even after photothermal treatment. However, tumors treated with the multifunctional therapeutic biological material almost disappeared on the 14th day after photothermal treatment. In summary, the multifunctional therapeutic biological material prepared in the examples of the present disclosure has excellent photothermal treatment of tumors in animals.

Figure 10:
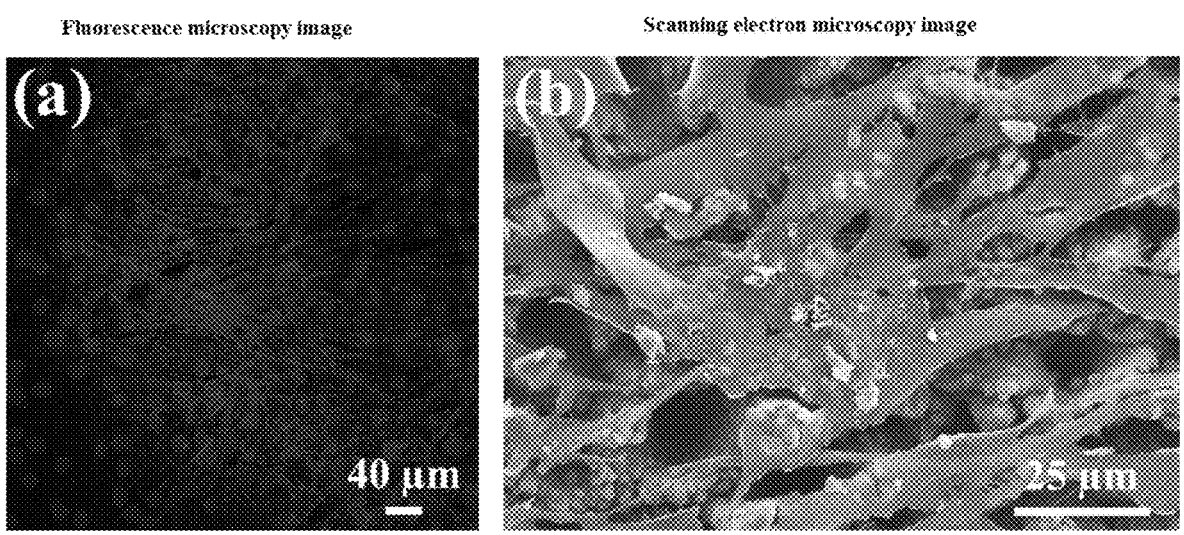
FIG. 10 shows an image of the adhesion of osteoblasts (MC3T3-E1, 7 days after co-cultivation) by the multifunctional therapeutic biological material prepared in the examples of the present disclosure; wherein (a) shows a fluorescence microscopy image; (b) shows a scanning electron microscopy image.

FIG. 10 shows the bone regeneration-inducing properties of the multifunctional therapeutic biological material prepared in the examples of the present disclosure. FIG. (a) shows a fluorescence microscopy image of the material and osteoblasts (MC3T3-E1) after co-culture for 7 days; and FIG. (b) shows a scanning electron microscopy image of the material and osteoblasts (MC3T3-E1) after co-culture for 7 days. It can be seen that the osteoblasts with abundant pseudopods almost completely cover the entire surface of the material, indicating that the multifunctional therapeutic biological material prepared in the examples of the present disclosure can significantly induce the adhesion and proliferation of osteoblasts, and has excellent osteogenic properties.

Figure 11:
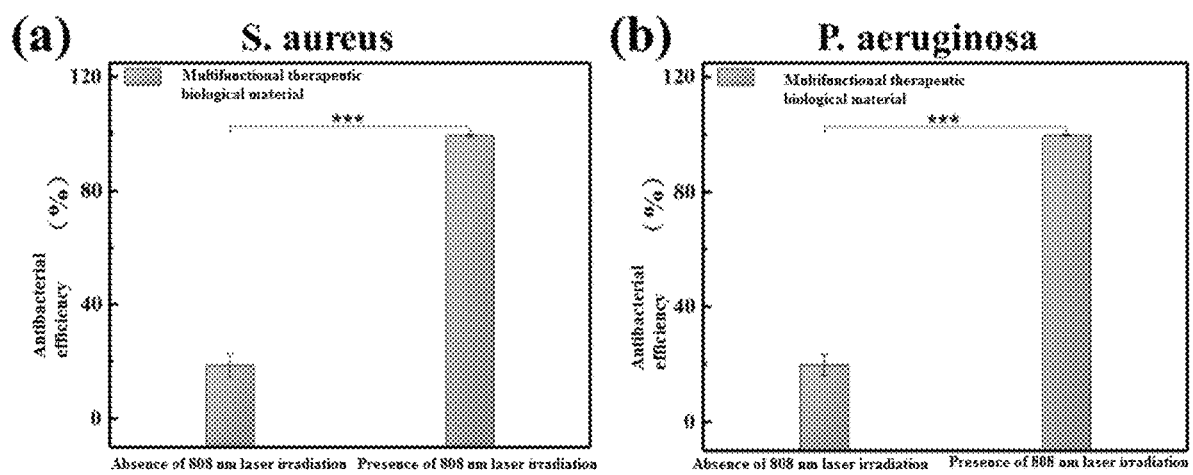
FIG. 11 shows the antibacterial efficiency of the multifunctional therapeutic biological material prepared in the examples of the present disclosure under the conditions of near-infrared (808 nm) laser power density of 1 W/cm$^2$ and continuous irradiation for 10 minutes; wherein (a) shows the antibacterial efficiency against *S. aureus*; and (b) shows the antibacterial efficiency against *P aeruginosa*.

FIG. 11 shows the antibacterial efficiency of the multifunctional therapeutic biological material prepared in the examples of the present disclosure under the conditions of a near-infrared (808 nm) laser power density of 1 W/cm$^2$ and continuous irradiation for 10 min. FIG. (a) shows the antibacterial efficiency of S. aureus; and FIG. (b) shows the antibacterial efficiency of P aeruginosa. It can be seen that the antibacterial efficiency can reach 99.5% against S. aureus, and 99.8% against P aeruginosa, indicating that the multifunctional therapeutic biological material prepared in the examples of the present disclosure can effectively inhibit a variety of bacterial infections.

The specific descriptions described above provide a further detailed description of the purpose, technical solutions and beneficial effects of the present disclosure. It should be understood that the foregoing descriptions are merely specific embodiments of the invention and are not intended to limit the protection scope of the present disclosure. Any modification, equivalent replacement, or improvement made within the spirit and principle of the present disclosure should be included in the protection scope of the present disclosure.

The invention claimed is:

1. A method for preparing a multifunctional therapeutic biological material, comprising:
   step 1: performing mirror polishing pretreatment on a surface of a biomedical material to be processed, ultrasonically cleaning it and drying it, to obtain a clean surface polishing material;
   step 2: preparing a large-area and consistent three-dimensional micro/nano composite structure on the surface of the surface polishing material obtained in step 1 by using femtosecond laser, cleaning the processed material with deionized water and drying it;
   step 3: preparing a nano-flower structure on the surface of the material obtained in step 2, and constructing a heterogeneous structure consisting of the three-dimensional micro/nano composite structure and the nano-flower structure; and
   step 4: putting the heterogeneous structure prepared in step 3 into a mixed solution containing gold ions and platinum ions, and by using ultraviolet light reduction method, reducing in situ into gold-platinum bimetallic nanoparticles on the heterogeneous structure to obtain the multifunctional therapeutic biological material.

2. The method according to claim 1, wherein the biomedical material in step 1 comprises a medical metal material, medical ceramic material, medical polymer material, and medical non-metal material.

3. The method according to claim 1, wherein the specific implementation steps of step 2 comprise:
   (1) fixing the clean surface polishing material on a glass slide, and fixing the glass slide on a high-precision six-degree-of-freedom translation stage;
   (2) modulating the traditional femtosecond laser into femtosecond laser double pulses in the time domain through splitting and combining or pulse shaping, with a time interval between two sub-pulses of 100 fs-100 ps and an energy ratio range of two sub-pulses of 0.1-10;
   (3) focusing the generated femtosecond laser double pulses on the surface of the surface polishing material by using an objective lens, and making sample move relative to the laser by controlling the high-precision six-degree-of-freedom translation stage through a computer control system; during processing, using high-pressure nitrogen for blowing chips and controlling laser flux, processing speed, processing distance, and double pulse delay time to prepare the three-dimensional micro/nano composite structure; and
   (4) cleaning the material after the above processing with deionized water and drying it.

4. The method according to claim 3, wherein the specific implementation steps of step 3 comprise:
(1) preparing a mixed solution consisting of sodium hydroxide solution and hydrogen peroxide solution as a hydrothermal reaction system;
(2) putting the biomedical material with a surface of the three-dimensional micro/nano composite structure prepared by the femtosecond laser double pulses processing into a bottom of a reactor, and then pouring the prepared mixed solution into the reactor for hydrothermal reaction; and
(3) cleaning the material after the hydrothermal reaction with deionized water and drying it.

5. The method according to claim 4, wherein the specific implementation steps of step 4 comprise:
(1) preparing a mixed solution consisting of chloroauric acid and chloroplatinic acid as a precursor solution;
(2) putting the biomedical material with a surface of the heterogeneous structure consisting of the three-dimensional micro/nano composite structure and the nanoflower structure prepared by the femtosecond laser double pulses processing combined with hydrothermal treatment into the bottom of a beaker, then adding the prepared precursor solution dropwise into the beaker, and finally placing an ultraviolet light source horizontally above the beaker for irradiation; and
(3) cleaning the material after photoreduction reaction with deionized water and drying it.

6. The method according to claim 3, wherein the multiple of the objective lens, laser flux, processing speed, processing distance, and double pulse delay time in step (3) are 5 times, 10 times or 20 times, 1-150 J/cm$^2$, 10-2000 μm/s, 2-30 μm and 5-20 ps respectively.

7. The method according to claim 4, wherein the concentration of the sodium hydroxide solution in step (1) is 1-20 mM, and the concentration of the hydrogen peroxide solution is 5%-30%.

8. The method according to claim 4, wherein the temperature of the hydrothermal reaction in step (2) is 50-120° C., and the reaction time is 24-48 h.

9. The method according to claim 5, wherein a concentrations of the chloroauric acid and the chloroplatinic acid in step (1) are both 10-50 mM, and the two solutions are mixed at 1:1 as the precursor solution; and the power of the ultraviolet light source in step (2) is 5-20 W, and the photoreduction process time is 10-30 s.

10. A method for treating tumors and bacterial infections and repairing bone defects, comprising administering to a subject in need thereof the multifunctional therapeutic biological material prepared by the method of claim 1.

11. A method for treating bone tumors and postoperative bacterial infections, comprising administering to a subject in need thereof the multifunctional therapeutic biological material prepared by the method of claim 1.

* * * * *

UNITED STATES PATENT AND TRADEMARK OFFICE
CERTIFICATE OF CORRECTION

PATENT NO. : 12,150,992 B2
APPLICATION NO. : 17/492060
DATED : November 26, 2024
INVENTOR(S) : Lan Jiang, Yunlong Ma and Jie Hu It is certified that error appears in the above-identified patent and that said Letters Patent is hereby corrected as shown below:

In the Claims

Claim 9, Column 12, Lines 13-14:
Replace "a concentrations" with --a concentration--.

Signed and Sealed this
Twenty-fifth Day of February, 2025

Coke Morgan Stewart
*Acting Director of the United States Patent and Trademark Office*